United States Patent [19]

Tetzlaff

[11] 4,029,967

[45] June 14, 1977

[54] DEVICE FOR THE UNIFORM IRRADIATION OF GOODS BY MEANS OF ELECTRO-MAGNETIC RADIATION

[76] Inventor: Karl-Heinz Tetzlaff, No. 3, Morikestrasse, Kelkheim, Germany

[22] Filed: Nov. 22, 1974

[21] Appl. No.: 526,187

[30] Foreign Application Priority Data

Nov. 24, 1973 Germany .......................... 2358652

[52] U.S. Cl. ........................... 250/492 R; 250/453; 250/454; 250/510
[51] Int. Cl.² ........................................ A61K 27/02
[58] Field of Search .......... 250/492, 453, 454, 455, 250/510

[56] References Cited
UNITED STATES PATENTS 3,496,362  2/1970  Kirkpatrick et al. .......... 250/492 X

*Primary Examiner*—Davis L. Willis
*Attorney, Agent, or Firm*—Lowe, King, Price & Markva

[57] ABSTRACT

An irradiation device for the uniform irradiation of goods by means of electro-magnetic radiation having a quantum energy larger than 5 KeV comprises at least one radiation source, means for the reception of goods to be irradiated, and at least one shielding element arranged laterally of the radiation path from the radiation source and the center axis of the goods in such a manner that the shielding effect of the shielding element increases with increasing lateral space from this radiation path. The radiation source, the shielding element and the means for the reception of the goods to be irradiated are arranged to allow for the radiation to enter the goods through the entire superficies thereof in such a way that the region immediately around the center axis of the goods is irradiated without radiation being affected by the shielding element.

9 Claims, 7 Drawing Figures

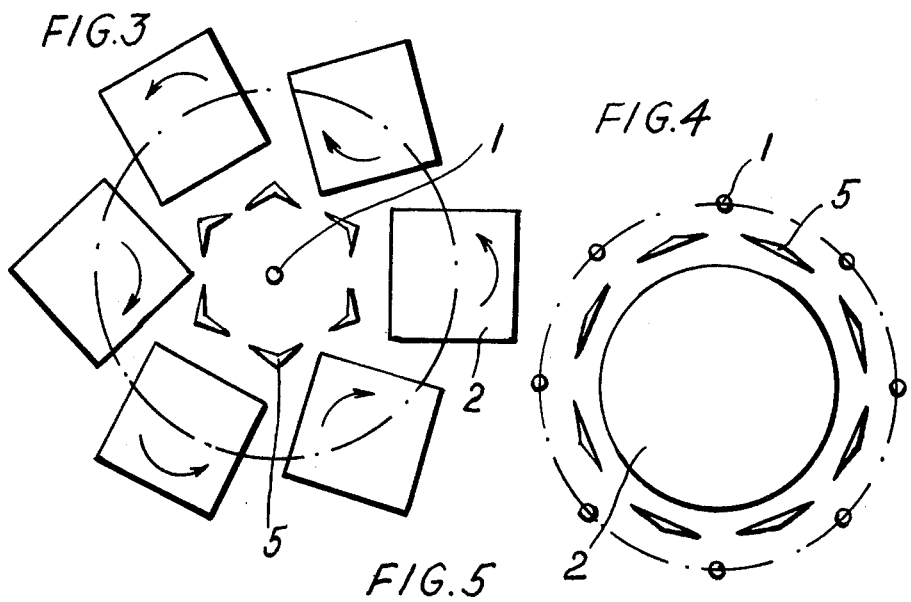
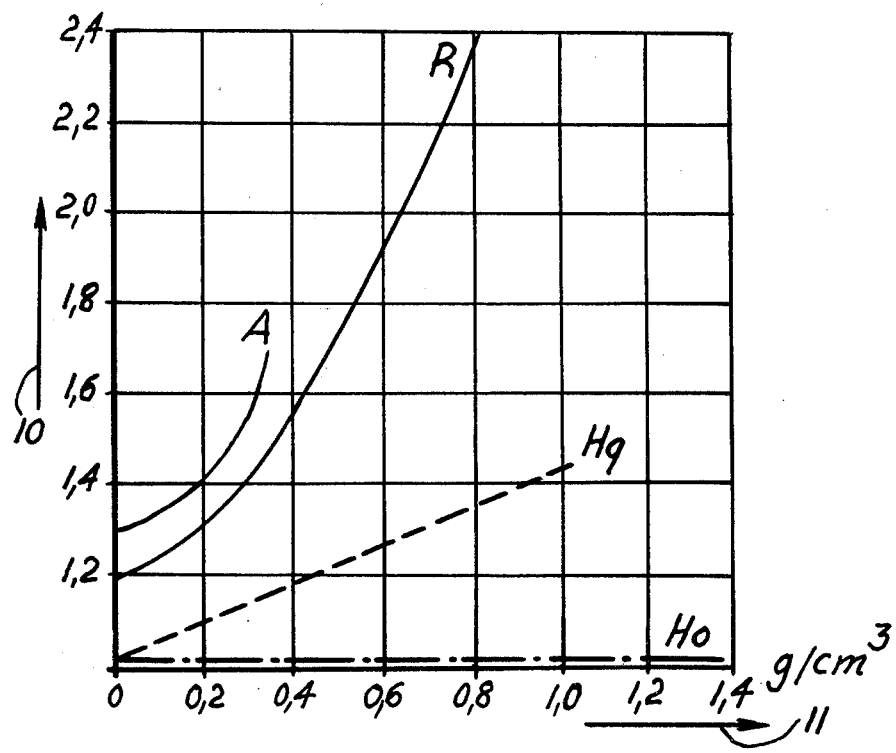

DEVICE FOR THE UNIFORM IRRADIATION OF GOODS BY MEANS OF ELECTRO-MAGNETIC RADIATION

BACKGROUND OF THE INVENTION

This invention relates to a device for the uniform irradiation of goods by means of electro-magnetic radiation having a quantum energy larger than 5 KeV.

Short-wave electro-magnetic radiation, as with X - or gamma rays, changes the physical, chemical and biological characteristics of materials. Technically, the radiation is applied in particular in the extinction of micro-organisms. Objects to be irradiated may include, for example, injection syringes, scalpels, suture material, feedstuffs, food for humans, and enzymic systems. This is often done in packages ready for shipment. A certain minimum dosage practically ensures sterility. Further irradiation would usually only injure the goods to be irradiated. In the technically common sizes of recipients in which the goods are normally treated, the spreading of the radiation and its absorption are the reasons why not every volume element receives the same dosage of irradiation. Even if, according to the state of the art, the recipients are being irradiated from several sides, considerable partial overdosages will be required to reach the minimum dosage necessary, e.g. for sterility. With some of the widely used plastics this leads to a reduction of material characteristics, as e.g. the increased embrittlement of polypropylen or the decoloration and smell development with polyvinylchloride. Furthermore, the overdosage leads also to a quality decrease in foods or to a considerable reduction for the biological effectiveness of enzymic systems. In the following, the relationship of largest dosage to smallest dosage in a certain material to be irradiated, e.g. irradiation containers like a cardboard box or a barrel, is called "overdosing ratio". Uniform irradiation means that the overdosing ratio will be close to 1.

There is a device known from the ATOMIC ENERGY OF CANADA LIMITED (in the following called "device A"), in which a number of cardboard boxes containing the goods to be irradiated and placed horizontally in two layers move around a $^{60}$Co radiation source in the shape of a 1 m$^2$ sized table in such a way that the cardboard boxes are radiated from two opposite sides. The cardboard boxes have to be turned after one half of the envisaged irradiation time has passed or the position of the track has to be changed. The overdosing ratio rises, e.g. for cardboard boxes of a size of 55.2 cm × 43.2 cm × 91.4 cm and a medium filling density (or packing density) of 0.3 g/cm$^3$, to values already too high for many applications.

Another device of the RADIATION DYNAMICS LIMITED (in the following called "device R") operates on the principle that six containers rotate on a circular path of 2.2 m in diameter around a $^{60}$Co rod-type source of approximately 45 cm length which moves up and down. The ashlar-type containers have each a square base and turn in the same direction around their axes. Rotation takes place in steps of 90°, so that practically one flat side is always directed towards the radiation source. Thus, the overdosing ratio with a given container size of for example 70 cm × 70 cm × 250 cm and a filling density of 0.7 g/cm$^3$ is larger than 2.

There are devices known for application in research (e.g. from ATOMIC ENERGY OF CANADA LIMITED) which have a number of rod-shaped radiation sources arranged in the form of a circle or use a X-ray cup anode. Apart from the volumes which are not uniformly irradiated at the axial ends, a cylindrical inner space is obtained in the center which has everywhere an almost constant dosage capacity. However, as soon as the goods to be irradiated are introduced into this inner space, the dosage capacity decreases considerably, especially in the case of objects of high density. This fact can be a great obstacle to research work.

The German patent specification 1.953,135 describes a device which operates on the basis of a radiation source having the shape of a table. The incorporation of a fadeout device consisting of prismatic rods leads to an improvement, as far as the decrease in dosage capacity with increasing distance normal to the radiation source is concerned. Otherwise this result is obtained only by means of a considerably larger plate-shaped radiation source. However, a somewhat more uniform irradiation always means that a reduced radiation efficiency has to be put up with, due to the prismatic rods.

However, the problem of producing a really uniform irradiation dosage in the goods to be irradiated, i.e., in matter, cannot be solved by means of creating a better and more homogeneous field of radiation in air — the common feature of the described known devices — not even by means of irradiation from several sides. The reason for this is that of the two values which influence the uniformity of the irradiation namely, the spreading of the radiation and the absorption of radiation, only the spreading of radiation is influenced. Thus the effect of the absorption of radiation which leads to the phenomenon that a dosage minimum occurs in the center of the goods to be irradiated, can in no case be compensated.

With the device according to the invention it is not endeavoured to create a homogeneous field of radiation in air. On the contrary, the field of radiation is intentionally considerably distorted, i.e., it is made more inhomogeneous. Surprisingly, it is thereby possible to compensate for the influence of the absorption of radiation. Thus, the goods to be irradiated are receiving the same radiation dosage in each volume element, which means there will be no dosage minimum in the center.

SUMMARY OF THE INVENTION

In order to avoid the disadvantages ensuing from the large overdosing ratio, it is the object of the present invention to provide a device of the type mentioned above which comprises at least one radiation source and means for the reception of goods to be irradiated at least one shielding element is arranged laterally of the radiation path from the radiation source and the center axis of the goods in such a manner that the shielding effect of the shielding element increases with increasing lateral space from the radiation path, radiation source, the shielding element and the means for the reception of the goods to be irradiated are arranged to allow for the radiation to enter the goods through the entire superficies thereof in such a way that the region immediately around the center axis of the goods is irradiated without radiation being affected by the shielding element. The shielding element laterally of the radiation path from the radiation source and the center axis of the goods to be irradiated ensures that in a cross section normal to the center axis of the goods, the dosage reached will be equal. If the goods are very large, it is recommended to arrange two shielding elements symmetrically on both sides of the radiation path. However, one source of radiation is sufficient, when the means for the reception of the goods are rotatably mounted. The goods to be irradiated rotate around their own axis, e.g. the axis of symmetry, or the radiation source and the lateral shielding element turn around the goods. A uniform irradiation of the cross section of the goods may also be obtained by grouping several radiation sources with their pertaining lateral shielding elements in the form of e.g. a circle around the goods which arrangement does not contain any moving parts.

In this description, a radiation source for X-rays is understood to be the place where the X-rays are produced. In contrast to the movement or arrangement of the radioactive radiation sources it is useful not to move the entire device for the production of X-rays or the anode, but to direct the beam of electrons producing the X-rays onto a rigid anode across electric or electro-magnetic fields. Thereby it is possible to produce a rotating or quasi rotating radiation source even without moved parts.

The above-mentioned term "center axis of the goods" means a rotating axis in the case of the turnable arrangement, and in the case of the static arrangement the crossing line of the beams of rays emitted from the various radiation sources and passing unhindered through the gap left by the shielding elements arranged laterally. Preferably the center axis of the goods coincides with the longest axis of symmetry of the goods.

In order to obtain a uniform irradiation across the entire volume of the goods to be irradiated, the means for the reception of the goods are mounted so as to be movable in the direction of the center axis of the goods. For example, if the goods are contained in barrels, the barrels rotate around their own axes and are passed with the aid of a conveyor belt in close sequence and with constant velocity past the radiation source. OPtimum use of radiation is obtained when several devices of this type surround the radiation source (or a beam of individual radiation sources) in the form of a circle. Only when changing over to a new charge of goods which does not correspond with the previous charge in density or irradiation dosage, irradiation will not be uniform for the first barrel.

Another possibility of obtaining uniform irradiation consists in arranging the radiation source and means for the reception of the radiation source and of the goods in such a way that the immission of rays in the central field between the axial ends of the goods is reduced. This reduction can be attained by setting up a long source of radiation standing preferably parallel to the center axis of the goods (e.g. longest axis of symmetry) so that the quantity of activity per unit of length will be smaller in the central region than opposite the axial ends of the goods, or that the center is shielded better than the ends. This shielding may consist in a reinforcement of the armoring surrounding the radiation source or of the container wall where and if the goods are placed in a container. It is even possible to obtain this shielding effect through parts of the goods to be irradiated. In this case, the container will have the shape of a barrel. The means for the reception of the radiation source and of the goods are equally suitable for the reduction of the useful radiation immission, if these permit to move a radiation source, which is geometrically small when compared with the dimensions of the goods, with respect to the center axis of the goods in such a manner that the exposure time for each unit of length of the axis of motion during one radiation cycle, which in this context may also mean "moving cycle", is smaller in the central field than in the space opposite the axial ends of the goods to be irradiated. If, e.g., the goods are continuously moved in containers past the radiation source, the exposure time has to be changed only at the beginning and at the end of a new charge. In addition to these three means for reducing the useful radiation immission in the central field (activity distribution, shielding and relative movement of the radiation source) the goods to be irradiated must be irradiated from all sides. As described above, this can be achieved by turning the goods or by having the radiation source turn around the goods to be irradiated. The same effect is also obtained if several radiation sources are arranged around the goods. This radiation technique for a uniform irradiation which operates without shielding elements introduced laterally into the radiation path from the source to the center axis of the goods, is limited to applications where density and thickness of the goods are not too great. However, as compared with known devices, a considerable reduction in the overdosing ratio is always obtained. (See also example).

However, if the attachments for the reduction of usable radiation immission and the shielding elements introduced laterally into the radiation path from the source and the center axis of the goods are arranged together in one device, goods of high density and great thickness to be penetrated can be irradiated with a uniformity unknown to this day. In this arrangement the goods which may have any wanted axial length do not have to be displaced in the direction of the center axis of the goods. Evidently, the devices described to ensure an irradiation from all sides have to be considered also in this arrangement. As far as the external shape of the goods to be irradiated is concerned, the cylindrical shape (barrel) is the most suitable, i.e., this shape provides a very uniform irradiation and a good radiation efficiency. When using different forms of cross sections for the containers accommodating goods, the overdosing ratio will be greater, but in many cases still acceptable.

In developing the device according to the invention, however, it is also possible to irradiate very uniformly also large and irregularly shaped goods, or goods in large containers of any required shape. However, this equipment may involve a reduced radiation efficiency, according to shape. The external container shape recommended is preferably a cylinder. In this cylinder, e.g. a container of square cross section is introduced whose inner space contains the goods to be irradiated. In this case, the space between cylinder and inner space is filled with material of the same filling density as the goods to be irradiated. By this method even large portions of meat or fish can be irradiated in a uniform manner, using water for the space between.

The device according to the invention enables the uniform irradiation of large volumes, e.g. cylinders of more than 1 m in diameter, and of high filling density goods, e.g. 1 g/cm$^3$. This has a considerable effect of technical rationalization, besides the considerable improvement in the quality of the goods, since nowaday there is a tendency to use larger packaging and shipping units (containers), and for these the device is easily adaptable.

X-ray equipments with low operating voltage and simple radiation protection may now be used also for considerably larger sizes of containers for goods to be irradiated, whenever short exposure time is important, or where the weight of the equipment should low, e.g. in non-stationary equipment.

Also maximum dosages of irradiation as prescribed by the authorities may be utilized to the full extent. In the case of foodstuffs, irradiation with the object of increasing their durability may lead to advantages in competition.

For example, a researcher who uses the device according to the invention with a uniformly irradiated inner space filled with water, when carrying out trials with irradiated foodstuffs, will have his work considerably facilitated because the food samples packed in plastic bags or in cans or bottles and which correspond approximately to the density of water, may be introduced into the radiation space in any required place and as closely together as necessary, without having to undertake complicated shielding calculations. In practice, this inner space is insufficiently used in the devices known up to now, because each new sample disturbs the rays to the other samples.

In contrast to the comparable known devices, the device according to the invention may also be used to improve the efficiency of the radiation (see also example), because the lateral shielding elements only reduce the radiation dosage, which, e.g. in the case of sterilization, is anyhow unnecessary; and because the axial ends of the goods, i.e., the usually underirradiated places to which, however, the minimum dosage refers, are brought up to the general dosage level needing a little more radiation only.

BRIEF DESCRIPTION OF THE DRAWINGS

Some preferred embodiments of the invention will now be described by way of example and with reference to the accompanying drawings, in which:

FIG. 3 is a top plan view of another embodiment for the irradiation of goods in containers having each a square base;

FIG. 4 is a similar view of still another embodiment having several radiation sources and a uniformly irradiated inner space, said embodiment comprising no moving parts;

FIG. 5 is a diagram showing the influence of filling density on the overdosing ratio;

DESCRIPTION OF THE PREFERRED EMBODIMENTS

Figure 1:
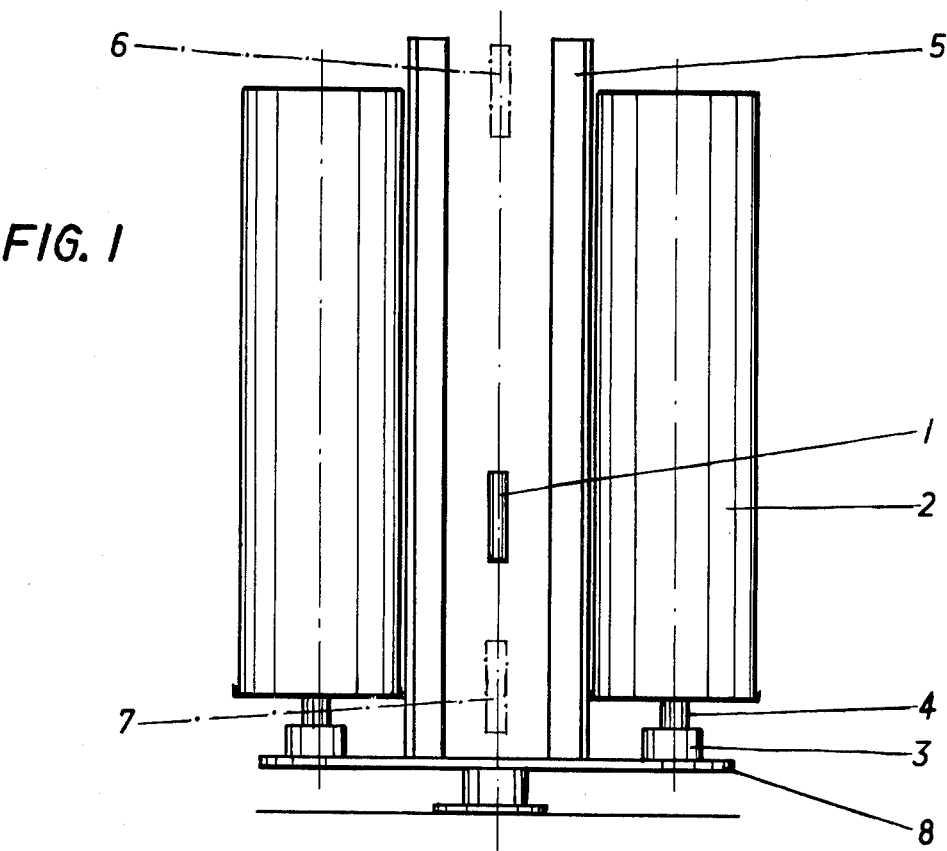
FIG. 1 is an elevational view of a device according to the invention.
Figure 2:
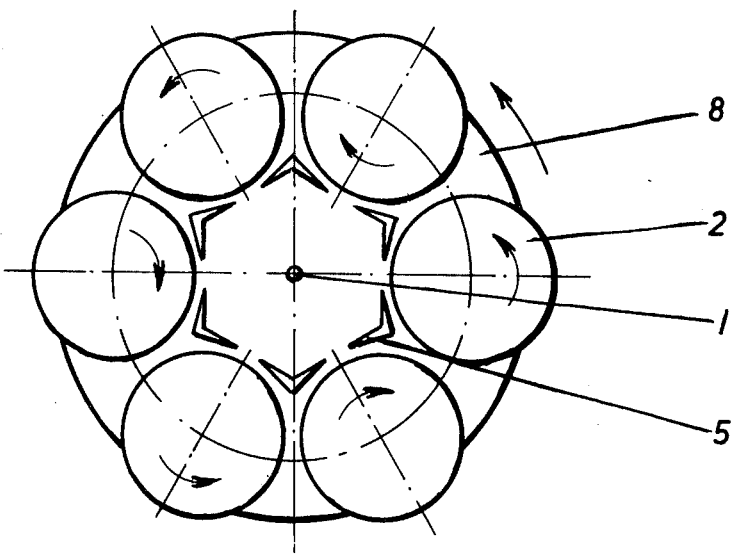
FIG. 2 is a top view of FIG. 1.

According to FIGS. 1 and 2 goods 2 to be irradiated are accommodated in six preferably cylindrical containers arranged in circular form around a rod-type radioactive radiation source 1. The containers are placed on a plate-shaped base and are moved in the same direction or preferably in opposite directions by means of a gear drive 3. The rotary plate shaft 4 should be a thin-walled hollow shaft. If necessary, the equipment can also be provided for goods hanging vertically.

Radiation which does not focus directly onto the center axis of the goods, is diminished increasingly with growing lateral space, by means of suitable shielding elements 5. In FIGS. 1 and 2 the shielding elements 5 of each two neighboring containers are expediently combined to form a unit. For small containers of goods to be irradiated, one shielding element for each container will be sufficient. The shielding elements 5 have to be adapted to the filling density of the goods and to the geometrical conditions involved. By this arrangement a uniform irradiation in a plane normal to the container axis is obtained. In order to be able to irradiate in a uniform manner also volume elements which are axially staggered, the preferably short rod-shaped radiation source 1 is moved in axial direction, parallel to the container axis, so that the exposure time per longitudinal unit — on a time average over one radiation cycle — is reduced in the central field, relatively to the end positions (in FIG. 1 denoted by 6 and 7), in the range opposite the container ends. A similarly good result may also be obtained if the exposure time is increased opposite the central field already before reaching the end positions. The source may be moved either continuously or step-by-step. This movement of the radiation source has to be optimized according to the container size and to the filling density of the goods. It has proved useful to arrange the containers of the goods to be irradiated together with the shielding elements 5 on a revolving disc 8 making a revolving or pendulum movement. This enables the use of several radiation sources of differing activity in one beam in the center, which is an advantage for the recharging of activity. Also, a revolving disc facilitates the charging and discharging of the goods 2 to be irradiated. Furthermore, the goods 2 may also consist of smaller units placed on top of each other or side by side.

FIG. 4 shows an embodiment which has no moving parts. Here a number of rod-shaped radiation sources 1 are arranged around the goods 2 to be irradiated. The goods 2 have the shape of a cylinder. Laterally of the path of rays from the radiation source and of the cylinder axis, two shielding elements 5 are associated with each radiation source. In this embodiment each two neighboring shielding elements 5 are combined to form a unit. The rod-shaped radiation sources 1 are somewhat longer than the cylinder-shaped goods and have at their ends more active quantity per longitudinal unit than in the central field. In the case of the radiation sources being formed by individual anode ranges of a X-ray equipment, the beam of electrons is guided analogous to the activity distribution so that at the ends a higher capacity is absorbed in the anode than in the central field.

The efficiency of radiation plays an important part in practical application. Efficiency of radiation means the portion of gamma radiation energy absorbed by the goods to be irradiated as compared with the amount of gamma radiation energy emitted from the nuclide. The portion of gamma radiation energy not used contains: self-absorption of the radioactive emitter, absorption of the source-capsule and other attachments, and the portion of radiation not utilizable for geometrical reasons. The following examples show that in the device according to the invention the self-absorption and the absorption in the material belonging to the radiation source is assumed to amount to 26%, normal to the radiation source axis. The rates in device R according to the state of the art can be regarded under the same aspects.

Figure 6:
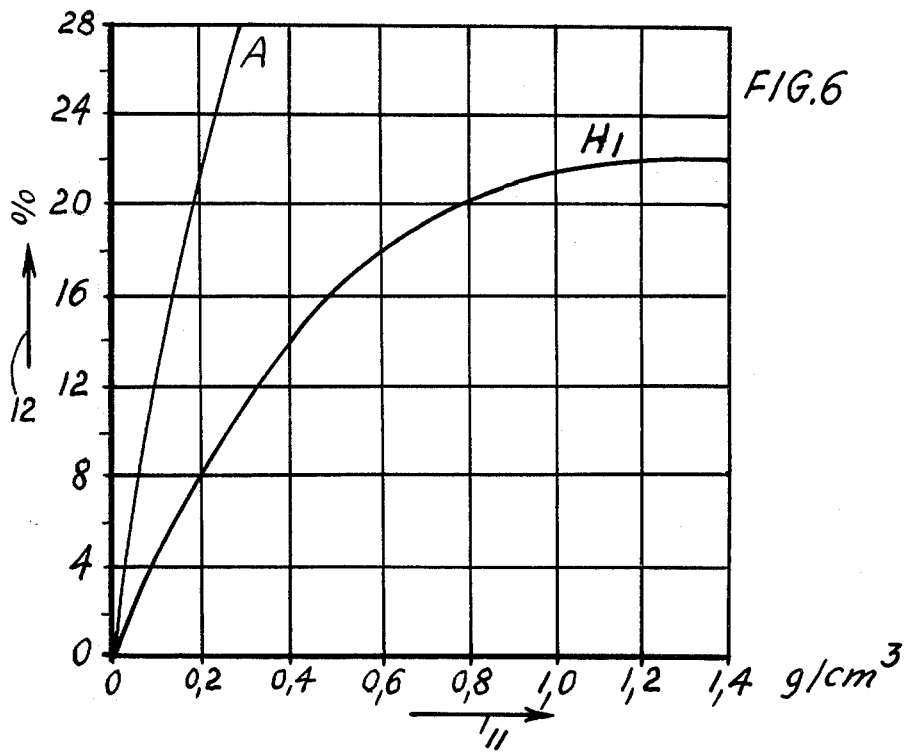
FIGS. 6 and 7 are diagrams showing the efficiency of rays as a function of the filling density by means of various examples.

EXAMPLE 1 a. As indicated in FIGS. 1 and 2, six cylindrical containers for goods to be irradiated are arranged around a rod-shaped 60 Co radiation source 46 cm in active length and 3 cm in diameter on a divided circle of 1 m in diameter. The thinplate containers for the goods have a diameter of 45 cm and a height of 200 cm, and are filled with fodder (filling density 0.7 g/cm$^3$). In practice three small containers will often be placed one on top of the other. The containers are placed on revolving plates which turn in opposite directions and are each mounted on a rotary plate shaft of thin-walled material. The space between the drive of the revolving plate and the support should not be smaller than about 10 cm. The lateral shielding elements are made of angle-iron in the shape illustrated. The outer angle-iron length is 14 cm, the maximum angle thickness is 2.4 cm. The inner angles are pointed and slightly concave, with a bending radius of 43 cm. They are arranged as shown in FIGS. 1 and 2, with the distance of the axis of the radiation source up to the 90° angle edge being 32 cm. The containers for the goods to be irradiated and the shielding elements are placed on a revolving disc which moves around the axis of the radiation source. The radiation source is driven step by step by means of a lifting gear, whereby 12 positions, at a distance of 16.7 cm each, are being approached one after the other beginning from the bottom. In the final positions opposite the container ends the radiation source has an exposure time longer than that at the other radiation source positions by a factor of 2.8. Several moving cycles may be applied within one radiation cycle. The overdosing ratio 10 in the goods to be irradiated is 1.04 (see curve $H_o$ in FIG. 5), the radiation efficiency 12 is 19%; (see curve $H_1$ in FIG. 6).

b. The device according to the invention in Example 1a) (container diameter 45 cm) is approximately comparable with the box dimensions 55.2 cm × 43.2 cm × 91.4 cm of the device A according to the state of the art, the value 43.2 cm standing for the thickness to be penetrated. Although the radiation utilization (FIG. 6, curve A) is very advantageous, the overdosing ratio with the filling density 11 of 0.7 g/cm$^3$ considered is intolerably high (FIG. 5, curve A). With the device according to the invention this material could be uniformly irradiated, even in containers with a diameter of 1.4 m.

Figure 7:
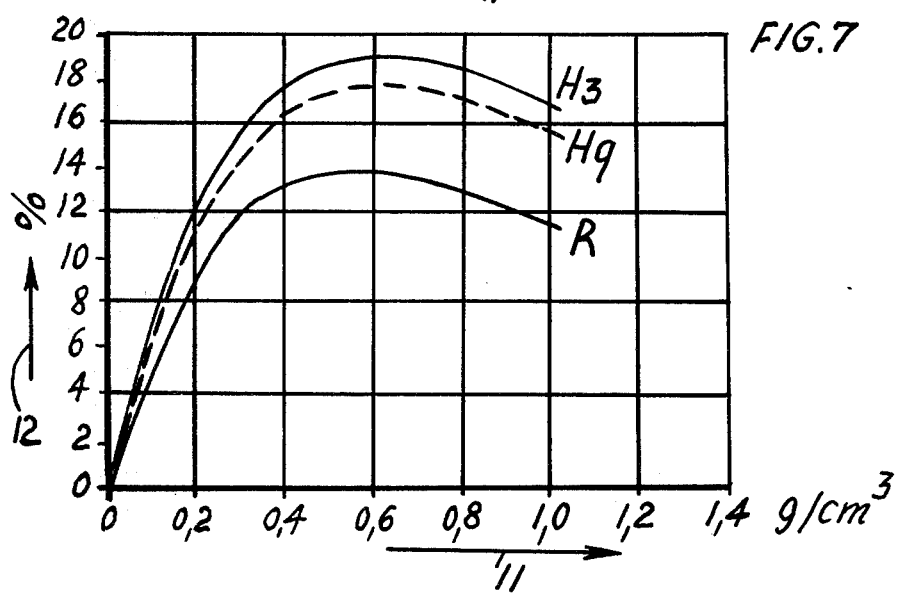

EXAMPLE 2 a. Six containers having each a square base are arranged on a divided circle 1.84 m in diameter on revolving plates turning constantly and synchronously in opposite directions, so that three containers turn one of their edges and the other three containers one of their flat sides to the radiation source (see also FIG. 3). The containers are made of thin steel sheet and have an edge length of 70 cm and a height of 250 cm. They are filled with goods having a filling density of 0.7 g/cm$^3$. In order to keep the overdosing ratio 10 as small as possible, the base and the cover of each container is reinforced with 3 mm steel sheet. The angle-iron shielding elements have a maximum side length of 23.5 cm and a maximum thickness of 3.2 cm. The inner sides of the angle point coniformly. The side edge has a distance of 48.5 cm from the axis of the source. The same arrangement is used for the radiation source as described in connection with Example 1a). Here twelve positions are approached, too. The strongest point of the radiation source is in the two end positions opposite the container ends. The exposure time in these end positions is higher than in the other positions by a factor of 3.6. The overdosing ratio 10 is 1.3 (curve $H_q$ in FIG. 5). The radiation efficiency 12 is 18% (curve $H_q$ in FIG. 7).

b. In comparison, there is a somewhat higher radiation efficiency 12 of 19% with cylindrical radiation containers having a diameter of 79 cm and a height of 250 cm (with the same volume as the square containers in example 2a) mounted on a divided circle 1.72 m in diameter (see curve $H_3$ in FIG. 7). The overdosing ratio 10 is about 1.04 (see curve $H_o$ in FIG. 5.). At the same time the cylindrical containers have a clear distance from each other which equals the minimum distance between the square containers in Example 2a).

c. Example 2a) is directly comparable with the device R according to the state of the art, since in both cases the same type of container and the same size of radiation container is used. According to curve R in FIG. 5 the overdosing ratio 10 in device R reaches already a value of 2.1 with the filling density 11 of 0.7 g/cm$^3$. The radiation efficiency 12 is about 13% (see curve R in FIG. 7)-.

From the results of Examples 2a) and 2c) it arises clearly that the device according to the invention represents an essential technological progress, as far as the efficiency of radiation and mainly the overdosing ratio is concerned. The low overdosing ratio of the device according to the invention as in Example 2a) is reached in that the radiation source opposite the container ends emits a higher radiation quantity (compare also table 1, section I to section II), and that in the device according to the invention shielding elements and continuous container rotation are used (see section III).

Table 1

Overdosing ratio for containers 70 cm × 70 cm × 250 cm with different filling densities of goods and different arrangements.

| Filling density → | 0.05 g/cm$^3$ | 0.7 g/cm$^3$ |
|---|---|---|
| I Source continuously up and down. Container rotation intermittently by 90° without shielding elements | 1.2 | 2.1 |
| II Source with increased radiation emission opposite the container ends, container rotation intermittently by 90° without shielding elements | 1.05 | 1.6 |
| III Source with increased radiation emission opposite the container ends, container rotation continuously with shielding elements | 1.03 | 1.3 |

Section I corresponds to the well-known device R. Section III corresponds to the device according to the invention as in Example 2a).

The invention may be embodied in other specific forms without departing from the spirit or essential characteristics thereof. The embodiments are therefore to be considered in all respects as illustrative and not restrictive.

What is claimed is:

1. An irradiation device for the uniform irradiation of goods by means of electro-magnetic radiation having a quantum energy larger than 5 KeV, comprising:
   a. at least one radiation source,
   b. means spaced from the radiation source for receiving goods to be irradiated, said goods having a center axis,
   c. a radiation path extending from the radiation source to the center axis of the goods,
   d. at least one shielding element laterally disposed with respect to the radiation path to provide a shielding effect that increases with increasing lateral space from the radiation path,
   e. the shielding element and the receiving means for the goods being arranged with respect to each other to allow for the radiation to enter the goods through the entire superficies thereof in such a way that the region immediately around the center axis of the goods is irradiated with radiation unaffected by the shielding element.

2. An irradiation device as claimed in claim 1, wherein
   at least one radiation source and at least one shielding element associated with said radiation source are arranged to rotate around the means for receiving the goods.

3. An irradiation device as claimed in claim 1, wherein
   the means for receiving the goods are rotatably mounted.

4. An irradiation device as claimed in claim 1, wherein
   a plurality of radiation sources and the shielding elements associated therewith are arranged in a circle around the means for receiving the goods to be irradiated,
   said radiation sources and said shielding elements being mounted so as to be stationary.

5. An irradiation device according to claim 1, wherein
   the receiving means for the goods to be irradiated includes means for effecting the continuous or step-by-step movement of the said goods in the direction of the center axis thereof.

6. An irradiation device as claimed in claim 1, wherein
   the receiving means for the goods to be irradiated comprise a container having a cylindrical shape,
   and said receiving means includes a space between the container wall and the goods,
   said space being filled with a material having the same filling density as the goods themselves.

7. An irradiation device for the uniform irradiation of goods by means of electro-magnetic radiation having a quantum energy larger than 5 KeV, comprising:
   a. at least one radiation source,
   b. means for receiving goods to be irradiated,
   c. said radiation source being small as compared with the dimensions of the goods to be radiated,
   d. means for moving the radiation source with respect to the goods to provide a radiation path between the source and the goods, and
   e. said moving means being effective to produce a smaller exposure time in the central field between the axial ends of the goods per unit of length of the axis of motion than at the axial ends of the goods.

8. An irradiation device for the uniform irradiation of goods by means of electro-magnetic radiation having a quantum energy larger than 5 KeV, comprising:
   a. at least one elongated radiation source movable along an axis of motion,
   b. means for receiving goods to be irradiated,
   c. said radiation source having a length corresponding approximately to the length of the goods, and
   d. shielding means providing a smaller quantity of activity per each unit of length of the axis of motion in the central field of the goods than at the ends of the goods.

9. An irradiation device for the uniform irradiation of goods by means of electromagnetic radiation having a quantum energy larger than 5 KeV, comprising:
   a. at least one radiation source for providing a radiation cycle,
   b. means for receiving goods having a central field between axial ends thereof, said goods to be irradiated during a radiation cycle of said radiation source,
   c. shielding means disposed between the radiation source and the center axis of the goods to be irradiated for reducing utilizable radiation immission in said central field,
   d. said radiation immission in said central field being less than at the ends of the goods.

* * * * *